United States Patent [19]

Buzby, Jr. et al.

[11] Patent Number: 4,559,178
[45] Date of Patent: Dec. 17, 1985

[54] RESOLUTION OF 3-BENZOYLTHIO-2-METHYL-PROPANOIC ACID WITH (+)-DEHYDROABIETYLAMINE

[75] Inventors: George C. Buzby, Jr., Penllyn; Henry G. Schouten, West Chester, both of Pa.

[73] Assignee: American Home Products Corporation, New York, N.Y.

[21] Appl. No.: 367,126

[22] Filed: Apr. 9, 1982

Related U.S. Application Data

[63] Continuation of Ser. No. 235,205, Feb. 17, 1981, abandoned, which is a continuation-in-part of Ser. No. 194,705, Oct. 6, 1980, abandoned.

[51] Int. Cl.$^4$ .............................................. C07C 153/07
[52] U.S. Cl. ................................................. 260/455 R
[58] Field of Search ...................................... 260/455 R

[56] References Cited

U.S. PATENT DOCUMENTS

| | | | |
|---|---|---|---|
| 3,644,479 | 2/1972 | Juby et al. | 560/102 |
| 4,046,889 | 9/1977 | Ondetti et al. | 260/455 R |
| 4,224,457 | 9/1980 | Iwao et al. | 560/102 |
| 4,294,775 | 10/1981 | McKinnie | 260/455 R |
| 4,346,045 | 8/1982 | De Heij | 260/455 R |
| 4,411,836 | 10/1983 | Ohashi et al. | 260/455 R |

FOREIGN PATENT DOCUMENTS 0008833  3/1980  European Pat. Off. .......... 560/102

OTHER PUBLICATIONS

Derwent Abstract No. 02816C of Japanese Patent Application No. 54-151912, published Nov. 29, 1979, to Santen Pharm. K.K.
S. H. Wilen, "Strategies in Optical Resolutions", Tetrahydron, 33, 2725-2736 (1977).
Mita et al., Chem. Abs., 89:46818g (1978).

*Primary Examiner*—Joseph Paul Brust
*Attorney, Agent, or Firm*—Arthur G. Seifert

[57] ABSTRACT

Disclosed herein is a process for the preparation of optically active compounds of the formula:

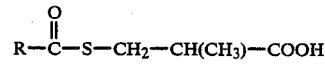

in which R is a lower alkyl, lower alkoxy, benzyloxy, phenyl, o-nitrophenyl, p-nitrophenyl, or p-tolyl group, or salts or esters thereof, which process comprises the following steps:

(a) starting with a racemic mixture of the compound of Formula I in which R is phenyl, namely, (+)-3-benzoylthio-2-methylpropanoic acid;

(b) adding thereto 0.40–0.60 moles of (+)-dehydroabietylamine per mole of (+)-3-benzoylthio-2-methyl-propanoic acid as the resolving agent, in the presence of an aliphatic carboxylic acid lower alkyl ester as the resolution solvent;

(c) crystallizing out and isolating the (−)-3-benzoylthio-2-methylpropanoic acid, (+)-dehydroabietylamine salt, which is dextrorotary;

(d) if necessary, recrystallizing said dextrorotary salt to further purify it;

(e) hydrolyzing the resulting dextrorotary salt with a base to separate the (+)-dehydroabietylamine resolving agent from the (−)-3-benzoylthio-2-methyl propanoate;

(f) hydrolyzing the (−)-3-benzoylthio-2-methylpropanoate with an acid to form the acid thereof;

(g) optionally, converting the phenyl group of the resulting (−)-3-benzoylthio-2-methyl-propanoic acid to one of the other R groups of Formula I.

3 Claims, No Drawings crystalline product is enhanced by using approximately one-half mole of the resolving agent per mole of the racemic starting material. Thus, 0.40–0.60 moles of (+)-dehydroabietylamine per mole of (±)-3-benzoulthio-2-methyl-propanoic acid are used, and, preferably, this range is 0.45–0.60 moles.

The (±)-3-benzoylthio-2-methylpropanoic acid starting material of step (a) is dissolved in the resolution solvent and kept at room temperature or slightly above (20°–30° C.). Separately, the (+)-dehydroabietylamine acetate (slightly over one-half mole per mole of starting material) is dissolved in the resolution solvent, and a small amount of water (0.05 ml/ml. of solvent) and triethylamine (a slight excess per mole of (+)-dehydroabeitylamine acetate) are added while keeping the temperature at 50°–55° C. The resolving agent solution is then quickly added to the starting material solution. After this mixing, the temperature remains at 40° C. and is kept there briefly during seeding. Then the temperature is lowered, first to 30° C. then to 20° C. The temperature of the mixture should not be held above 40° C. or at 40° C. for very long in order to avoid decomposition.

The recrystallization of step (d) is preferably carried out from denatured ethanol which is preheated to 70°–75° C. to avoid applying excess heat to the (−)-3-benzoylthio-2-methyl-propanoic acid, (+)-dehydroabietylamine salt formed in step (c). The other recrystallization solvents described above, may also be used for recrystallization with appropriate changes of temperatures and times.

The base used in step (e) to hydrolyze the salt and remove the resolving agent is preferably added in a stepwise fashion until all the solids dissolve or the pH reaches 10.5. pH's above this level should be avoided since the product may decompose under these conditions. For this reason only 1N sodium hydroxide is preferred. Other alkali metal or alkaline earth hydroxide bases may also be used with the same strength limitation. Likewise, in the acid hydrolysis step (f), dilute (1N) acid is used to prevent decomposition of the final product. The acid is added slowly until the pH reaches 3. The extraction solvent for steps (e) and (f) may be methylene chloride, ether or any other suitable solvent for the resolving agent. It will be appreciated that the (+)-dehydroabietylamine base extracted in step (e) may be isolated and reused.

As first stated, the R groups other than phenyl may be obtained from the phenyl derivative (i.e. from the resolved 3-benzoylthio-2-methyl propanoic acid) by processes well-known to those skilled in the art. The R group "lower alkyl" means alkyl groups having 1–6 carbon atoms, for example, hexyl, t-butyl, iso-butyl, n-butyl, isopropyl, n-propyl, ethyl, or methyl; of which methyl and t-butyl are preferred. The R group "lower alkoxy" means alkoxy groups having 1–6 carbon atoms in the hydrocarbon chain, for example, t-butoxy, iso-butoxy, n-butoxy, isopropoxy, n-propoxy, ethoxy or methoxy; of which t-butoxy is preferred.

EXAMPLE I

A. Preparation of
(−)-3-benzoylthio-2-methyl-propanoic acid,
(+)-dehydroabietylamine salt (±)-3-Benzoylthio-2-methyl propanoic acid (18.00 g.) (.08 m.) in ethyl acetate (300 ml.) as added to (+)-dehydroabietylamine (12.54 g.) (0.044 m.) in ethyl acetate (300 ml.), and the mixture was allowed to stand at room temperature for 1 hour. Filtration, washing with a small amount of cold ethyl acetate and drying provided crude (−)-3-benzoylthio-2-methyl-propanoic acid, (+)-dehydroabietylamine salt (19.55 g., m.p. 151°–153° C.). This material was purified by adding to boiling methyl acetate (2000 ml.) and the minute solution was effected, chilling in an ice bath. After standing at +10° C. for 2 hours, the precipitated solid was filtered and dried to provide the pure salt (11.925 g., m.p. 157°–159° C.).

B. Regeneration of
(−)-3-benzoylthio-2-methyl-propanoic acid

This salt was partitioned between ether (200 ml.) and ice water (300 ml.) containing 2N aq NaOH (11.7 ml.) and the aqueous layer was separated and filtered. This aqueous layer was acidified with dilute HCl in the cold, the precipitated oil was extracted 2 times with ether (200 ml.), and the ether was dried (Na$_2$SO$_4$) and evaporated. The residue was crystallized from pentane containing ether to provide (−)-3-benzoylthio-2-methyl-propanoic acid (3.485 g., m.p. 63°–65° C.), $[\alpha]_D^{26°} = -40.42°$ (C=2.2, EtOH) (38.7% yield).

EXAMPLE II

A. Preparation of
(−)-3-benzoylthio-2-methyl-propanoic acid,
(+)-dehydroabietylamine salt To 1500 ml. of ethy acetate at 50°–55° C. was added 75 ml. of water and 54 ml. of triethylamine (39.2 g.; 0.387 moles). Keeping the temperature at 50°–55° C., (+)-dehydroabietylamine acetate (DHAA) (127 g.; 0.368 moles) was added in portions under stirring until dissolved. In a separate flask, the (±)-3-benzoylthio-2-methyl-propanoic acid (BTMPA) (150 g.; 0.669 moles) was dissolved in 1500 ml. of ethyl acetate under nitrogen while heating the mixture to 30° C. The DHAA solution was added as quickly as possible to the BTMPA solution, after which the temperature of the mixture was 40° C. This temperature was maintained for 10 minutes during seeding; then the mixture was cooled to 30° C. over 30 minutes and further to 20° C. over 30 minutes and stirred at this temperature for an additional 30 minutes. The solids were filtered out, reslurried in 500 ml. of ethyl acetate at room temperature, filtered again, washed with ethyl acetate, and sucked as dry as possible.

3000 Ml. of ethanol 3A anhydrous were heated under nitrogen to 70°–75° C. and the wet BTMPA-DHAA salt cake was added thereto and stirred while heating at reflux for 5 minutes. Solids were filtered out in a large Buchner funnel under light suction after cooling to 70°, using ethanol 3A preheated to about 60° C. as a rinse. The resulting filtrate was transferred to a clean flask under nitrogen and reheated to 55°–60° until the solids were again dissolved. Seeding then took place at 55° C. and slow stirring. The solution was then cooled to 40° over 30 minutes; then further to 30° over 30 minutes; then to 20° over 30 minutes; and finally put in an ice bath for one hour. Thereafter, the solution was filtered and washed with some of the filtrate and again with 75 ml. of ethanol 3A anhydrous and dried at 35°–45° C. to a constant weight to provide pure (−)-3-benzoylthio-2-methyl propanoic acid, (+)-dehydroabietylamine salt (93.0 g.), m.p. 153°–153.5°, $[\alpha]_D^{25°} = +16.2°$ (C=2, THF), 54.5% yield.

RESOLUTION OF 3-BENZOYLTHIO-2-METHYL-PROPANOIC ACID WITH (+)-DEHYDROABIETYLAMINE

This application is a continuation of application Ser. No. 235,205, filed Feb. 17, 1981 which in turn is a continuation-in-part of application Ser. No. 194,705, filed Oct. 6, 1980, both of which are now abandoned.

The invention relates to a process for obtaining optically active 3-benzoylthio-2-methyl-propanoic acid utilizing (+)-dehydroabietylamine as a resolving agent. Other optically active derivatives of this acid may be obtained by converting the terminal phenyl group to other groups in a conventional manner. Further, the invention includes the (−)-3-benzoylthio-2-methyl-propanoic acid, (+)-dehydroabietylamine salt which is formed during the resolution process.

(−)-3-Benzoylthio-2-methyl-propanoic acid and the derivatives thereof described in Formula I below are useful as intermediates in the synthesis of the class of antihypertensive agents known as angiotensin converting enzyme (ACE) inhibitors. An example of an ACE inhibitor which may be made from the resolved compound is the proline derivative 1-(3-mercapto-2D-methylpropanoyl)-L-proline which is described in U.S. Pat. No. 4,105,776.

In carrying out chemical resolutions of racemates, the purity of the initial crystalline product is crucial to the resolution and is dependent on the resolving agent, the solvent, and the reaction conditions. Although various optically active amines such as (±)-α-methylbenzylamine, (+)-α-(1-naphthyl)ethylamine, and 1-ephedrine form salts with the (±)-benzoylthio-2-methyl-propanoic acid, only the (+)-dehydroabietylamine salt was of sufficient optical purity to afford complete separation of enantiomers after one or two recrystallizations. Moreover, the salt formed was with the desired 1(−)enantiomer. The purity of the initial crystalline product (as demonstrated by the purity of the final product) was also substantially enhanced by the use of one-half mole of the (+)-dehydroabietylamine resolving agent per mole of (±)-3-benzoylthio-2-methyl-propanoic and the selection of an aliphatic carboxylic acid lower alkyl ester as the resolution solvent. Even in larger scale runs (100 grams or more of starting material) this process gave (−)-3-benzoylthio-2-methyl-propanoic acid having high optical purity ($[\alpha]25/D = -41.4°$ to $-42.7°$, AT-147, 2% ethanol) with high yields (in excess of 45 percent overall) after only one recrystallization.

A further obstacle to the resolution of β-thioesters of carboxylic acids is their tendency to form acrylic acids by hydrolysis or elimination reactions. Surprisingly, however, the benzoyl group present in the instant compound imparts sufficient stability to the molecule in order for it to survive both the conditions of recrystallization and the contact with acid and base in the subsequent regeneration step. Additionally, the (−)-3-benzoylthio-2-methyl-propanoic acid generated by the hydrolyses is subject to decomposition in excess alkali.

The process of the invention is for the preparation of optically active compounds of the formula:

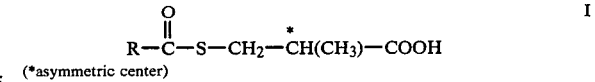

(*asymmetric center)

in which R is a lower alkyl, lower alkoxy, benzyloxy, phenyl, o-nitrophenyl, p-nitrophenyl, or p-tolyl group, or salts or esters thereof, which process is characterized by the following steps:
(a) starting with a racemic mixture of the compound of Formula I in which R is phenyl, namely, (±)-3-benzoylthio-2-methyl-propanoic acid;
(b) adding thereto 0.40–0.60 moles of (+)-dehydroabietyl-amine per mole of (±)-3-benzoylthio-2-methyl-propanoic acid as the resolving agent, in the presence of an aliphatic carboxylic acid lower alkyl ester as the resolution solvent;
(c) crystallizing out and isolating the (−)-3-benzoylthio-2-methyl propanoic acid, (+)-dehydroabietylamine salt, which is dextrorotary;
(d) if necessary, recrystallizing said dextrorotary salt to further purify it;
(e) hydrolyzing the resulting dextrorotary salt with a base to separate the (+)-dehydroabietylamine resolving agent from the (−)-3-benzoylthio-2-methyl propanoate;
(f) hydrolyzing the (−)-3-benzoylthio-2-methyl-propanoate with an acid to form the acid thereof;
(g) optionally, converting the phenyl group of the resulting (−)-3-benzoylthio-2-methylpropanoic acid to one of the other R groups of Formula I.

The (±)-3-benzoylthio-2-methylpropanoic acid starting material is made in a conventional manner by reacting thiobenzoic acid with methacrylic acid. The reaction is carried out in acetone, and the reaction mixture is refluxed for 5 hours. The resulting product is partitioned between hexane and the acetone. The acetone is removed and the hexane solution is cooled to 0°–5° C. to form the product as a crystalline precipitate.

The initial salt formation described in step (c) above is carried out in aliphatic carboxylic acid lower alkyl esters, the "resolution solvent". The acid portion of such esters may have one to four carbon atoms, such as isobutyric, butyric, propionic, or acetic acid. Similarly, the alcohol portion of such ester may have one to four carbon atoms, such as t-butyl, s-butyl, isobutyl, n-butyl, isopropyl, n-propyl, ethyl, or methyl alcohol. Of these esters, ethyl acetate and methyl acetate are most preferred, and ethyl or butyl formate are also preferred. The recrystallization of step (d) may be carried out in an aliphatic carboxylic acid lower alkyl ester, a lower alkanol, a lower ketone, tetrahydrofuran, or acetonitrile. Of these recrystallization solvents, methyl acetate and denatured ethanol are preferred. The lower alkanol may have one to four carbon atoms as just described above. The lower alky ketones also consist of alkyl groups having one to four carbon atoms, such as butyl methyl, diethyl, and ethylmethyl ketone or, preferably, acetone.

The (+)-dehydroabietylamine resolving agent may be prepared beforehand as the free base, or it may be added as the acetate. In the latter case, another base (e.g. triethylamine) is added to the initial reaction mixture to remove the acetate. (+)-Dehydroabietylamine acetate is available commercially and its use or conversion to the free base are well-known to those skilled in the art. As described above, the purity of the initial The filtrate was concentrated under vacuum to approximately 500 ml. at 35°-40° C., then coled to 0°-5° C. Filtering, washing the solid and drying gave an additional 15 g. (8.8%) of the salt, m.p. 149°-150° C.

B. Regeneration of (−)-3-benzoylthio-2-methylpropanoic acid (−)-3-Benzoylthio-2-methyl-propanoic acid, (+)-dehydroabietylamine salt (100 g.; 0.196 moles) was partitioned between methylene chloride (400 ml.) and water (400 ml.) with 100 ml. of 1N sodium hydroxide solution. An additional 100 ml. of 1N sodium hydroxide was added to adjust the pH to between 10.2 and 10.5 and dissolve the solids. The liquids were filtered in order to break the emulsion formed. The layers of liquid were separated and the methylene chloride layer was washed with 100 ml. of water and the combined aqueous layers were then washed with 100 ml. of methylene chloride.

The aqueous layer was then brought to a pH of 3 with successive 100 ml. aliquots of 1N hydrochloric acid. The oil that formed was extracted with 150 ml. of methylene chloride, and the aqueous layer washed twice with 50 ml. of methylene chloride. The methylene chloride extracts were combined and washed with 50 ml. of water, and the organic extract was filtered. The filtrate was admixed with 400 ml. of hexane and this was concentrated under stirring and reduced pressure to 400 ml. at pot temperatures not exceeding 35°-40° C. This dilution with 400 ml. of hexane and concentration down to 400 ml. was repeated again. Thereafter, the mixture was cooled to 20°-25° C. and stirred slowly for one hour. The solids were filtered out and washed 2 times with 25 ml. of hexane and then dried in a vacuum oven below 55° C., yielding the product (−)-3-benzoylthio-2-methyl-propanoic acid, 36.6 g. (83.2% yield); m.p. 68.5°-69.5° C., $[\alpha]_D^{25°} = -42.4°$ (C=2 in EtOH).

EXAMPLE III

A. Preparation of (−)-3-benzoylthio-2-methyl-propanoic acid, (+)-dehydroabietylamine salt 3670 Ml. of ethyl acetate were heated to 50°-55° C. in a 6000 ml. Erlenmeyer flask furnished with a magnetic stirrer. To this, were added 184 ml. of water and 132.3 ml. of tirethylamine. While maintaining the temperature at 50°-55° C., 311.2 g. (0.901 moles) of dehydroabietylamine acetate (DHAA) were added in portions and stirred until dissolved.

Separately, in a 4 neck 12 l. flask furnished with a stirrer, thermometer, nitrogen inlet and condenser, 367 g. (1.615 moles) of (±)-3-benzoylthio-2-methyl-propanoic acid (BTMPA) were dissolved in 3670 ml. of ethyl acetate while maintaining the temperature at 30° C. To this solution, the previously prepared DHAA-ethyl acetate solution as added as quickly as possible. The temperature after the addition was completed was 40° C. which was held for 10 minutes during seeding. The mixture was then cooled to 30 over 30 minutes and further to 20° C. over another 30 minutes, and finally stirred at 20° C. for 30 minutes. The solids were then filtered out and reslurried in 1225 ml. of ethyl acetate at room temperature. The solids were filtered again and washed with 184 ml. of ethyl acetate and sucked as dry as possible.

A 12 l. four necked flask was furnished with a stirrer, a nitrogen inlet, a thermometer, and a reflux condenser. Under a slight nitrogen gas flow 5 l. of ethanol 3A anhydrous were added to the flask and heated to 70°-75° C. The wet BTMPA-DHAA salt cake was added at this temperature and then the mixture was heated to reflux for about 5 minutes after which solution was affected.

The temperature of the solution was reduced to 55° C. and the stirring speed was reduced to slow, and the solution was seeded. The solution was then cooled successively over 30 minute periods to 40°, 50° and 20° C. and, finally, kept in an icebath overnight.

The solids were filtered and washed with some filtrate and then with 184 ml. of ethanol 3A anhydrous. The solid product was then dried in a vacuum oven at 35°-45° C. to a constant weight, giving 246 g. 59.2 percent yield of (−)-3-benzoylthio-2-methyl-propanoic acid, (+)-dehydroabietylamine salt, m.p. 156°-7° C.

B. Regeneration of (−)-3-benzoylthio-2-methyl-propanoic acid

984 Ml. of methylene chloride, 984 ml. of water and 246 ml. (.246 moles) of 1N sodium hydroxide were mixed in a 4 l. beaker under magnetic stirring. To this mixture was added the (−)-BTMPA-(+)-DHAA salt (246 g.) obtained above. Thereafter, another 246 ml. of 1N sodium hydroxide was added, and the mixture was stirred for ten minutes while adjusting the pH to 10.2-10.5.

The resulting aqueous and methylene chloride layers were separated, and the methylene chloride layer was washed with 246 ml. of water. The aqueous layers were combined and washed with 246 ml. of methylene chloride. 496 Ml. of 1N hydrochloric acid were added to the aqueous layer (pH=3). The oil which separated out was extracted with 369 ml. of methylene chloride, and the aqueous layer was washed once more with 123 ml. of methylene chloride. The extracts were combined and washed with 125 ml. of water, and the organic extract was filtered.

The filtrate was transferred to a 3 l. 3 necked flask furnished with a condenser, a stirrer and a thermometer, and 984 ml. of hexane were added. The solution was concentrated under reduced pressure to 984 ml. while keeping the pot temperature at 55°-40° C. This dilution with 984 ml. of hexane and concentration down to 984 ml. was repeated once. Thereafter, the solution was cooled to 20°-25° C. and held at that temperature for 60 minutes. The solids were filtered out and washed twice with 61.5 ml. of hexane. The resulting solid was dried in a vacuum oven at temperatures below 35° C. yielding the product (−)-3-benzoylthio-2-methyl-propanoic acid, 94 g. (86.8 percent yield in step B, 51.4 percent overall yield); m.p. 69.7° C.; $[\alpha]_D^{25°} = -42.3$ (AT-147; 2% ethanol).

We claim:

1. A process for the resolution of (±)-3-benzoylthio-2-methyl-propanoic acid to obtain the (−)isomer thereof, which process comprises the following steps:
   (a) starting with a racemic mixture of said (±)-3-benzoylthio-2-methyl-propanoic acid;
   (b) adding thereto 0.40-0.60 moles of (+)-dehydroabietylamine per mole of (±)-3-benzoylthio-2-methyl-propanoic acid as the resolving agent, in the presence of an aliphatic carboxylic acid lower alkyl ester, the acid and alcohol portions of which are lower alkyl groups of 1 to 4 carbon atoms, as the resolution solvent;

(c) crystallizing out and isolating the (−)-3-benzoylthio-2-methyl-propanoic acid, (+)-dehydroabietylamine salt, which is dextrorotary;

(d) hydrolyzing the resulting dextrorotary salt from (c) with a base to separate the (+)-dehydroabietylamine resolving agent from the (−)-3-benzoylthio-2-methyl propanoate; and (e) hydrolyzing the (−)-3-benzoylthio-2-methyl-propanoate with an acid to form the acid thereof.

2. A process according to claim 1 wherein the range of moles of (+)-dehydroabietylamine is 0.45–0.60.

3. A process according to claim 1 wherein the aliphatic carboxylic acid lower alkyl ester is selected from ethyl acetate or methyl acetate.

* * * * *